(12) United States Patent
Xu et al.

(10) Patent No.: US 11,253,446 B2
(45) Date of Patent: *Feb. 22, 2022

(54) STABLE METAL ION CONTAINING COMPOSITIONS

(71) Applicant: Colgate-Palmolive Company, New York, NY (US)

(72) Inventors: Yun Xu, Langhorne, PA (US); Xiao Yi Huang, Guangzhou (CN); Yuan Hui Xie, Guangzhou (CN); Xiong Fei Qin, Zengcheng (CN)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/719,693

(22) Filed: Dec. 18, 2019

(65) Prior Publication Data

US 2020/0121571 A1 Apr. 23, 2020

Related U.S. Application Data

(63) Continuation of application No. 15/954,816, filed on Apr. 17, 2018, now Pat. No. 10,548,823, which is a continuation of application No. 14/653,214, filed as application No. PCT/CN2012/086819 on Dec. 18, 2012, now Pat. No. 9,968,528.

(51) Int. Cl.
*A61K 8/24* (2006.01)
*A61K 8/365* (2006.01)
*A61K 8/73* (2006.01)
*A61K 8/27* (2006.01)
*A61Q 11/00* (2006.01)

(52) U.S. Cl.
CPC .................. *A61K 8/24* (2013.01); *A61K 8/27* (2013.01); *A61K 8/365* (2013.01); *A61K 8/73* (2013.01); *A61K 8/731* (2013.01); *A61Q 11/00* (2013.01); *A61K 2800/48* (2013.01)

(58) Field of Classification Search
CPC .......... A61K 8/731; A61K 8/24; A61K 8/365; A61K 8/27; A61K 8/73; A61K 2800/48; A61Q 11/00

See application file for complete search history.

(56) References Cited

U.S. PATENT DOCUMENTS

| | | | |
|---|---|---|---|
| 8,852,559 B2 | 10/2014 | Porter et al. | |
| 8,974,772 B2 | 3/2015 | Fruge et al. | |
| 9,579,269 B2 | 2/2017 | Mello et al. | |
| 9,682,256 B2 | 6/2017 | Boyd et al. | |
| 2006/0141072 A1 | 6/2006 | Arvanitidou et al. | |
| 2009/0202450 A1 | 8/2009 | Prencipe et al. | |
| 2009/0202454 A1 | 8/2009 | Prencipe et al. | |
| 2009/0269287 A1 | 10/2009 | Berta | |
| 2012/0020897 A1 | 1/2012 | Campbell et al. | |
| 2012/0308488 A1 | 12/2012 | Pilch et al. | |
| 2013/0330283 A1 | 12/2013 | Vogt et al. | |

FOREIGN PATENT DOCUMENTS

| | | |
|---|---|---|
| CN | 101690699 | 4/2010 |
| CN | 102283794 | 12/2011 |
| CN | 102379827 | 3/2012 |
| CN | 102451118 | 5/2012 |
| CN | 102579292 | 7/2012 |
| CN | 102781519 | 11/2012 |
| EP | 0528458 | 2/1993 |
| EP | 1085852 | 3/2001 |
| EP | 1830821 | 9/2007 |
| GB | 1097075 | 12/1967 |
| RU | 2447879 | 4/2012 |
| WO | 1999/053893 | 10/1999 |
| WO | 2002/045678 | 6/2002 |
| WO | 2004/069170 | 8/2004 |
| WO | 2007/037960 | 4/2007 |
| WO | 2010/141693 | 12/2010 |
| WO | 2011/094505 | 8/2011 |

OTHER PUBLICATIONS

Corresponding Office Action issued by the Colombian Patent Office dated Apr. 19, 2016.
International Search Report and Written Opinion in International Application No. PCT/CN2012/086819, dated Oct. 10, 2013.

*Primary Examiner* — Lezah Roberts

(57) ABSTRACT

Disclosed herein are oral care compositions comprising: a) one or more pyrophosphate compounds, wherein the total concentration of pyrophosphate compounds in the composition is 0.5 wt % to 1.5 wt %, based on the weight of the oral care composition; b) one or more thickening gums, wherein the total concentration of thickening gums in the composition is 1.25 wt % to 1.6 wt %, based on the weight of the oral care composition; and c) a metal ion source.

17 Claims, No Drawings

STABLE METAL ION CONTAINING COMPOSITIONS

CROSS-REFERENCE TO RELATED APPLICATIONS

This application is a continuation of U.S. application Ser. No. 15/954,816, filed on Apr. 17, 2018, which is a continuation of U.S application Ser. No. 14/653,214, filed on Jun. 17, 2015, which is a National Stage Application under 35 C.F.R. 371 of International Application No. PCT/CN2012/086819, filed on Dec. 18, 2012, the contents of each of which are incorporated herein by reference in their entirety.

BACKGROUND

Chelating agents are sometimes used in order to reduce the metallic taste and astringency of oral care compositions containing a metal ion source. Tetrasodium pyrophosphate (TSPP) and tetrapotassium pyrophosphate (TKPP) are two commonly used chelating agents.

However, it has been observed that such dentifrice compositions containing efficacious amounts of TSPP and TKPP as chelating agents exhibit phase separation when the dentifrice base includes certain commonly used thickening gum systems.

A need therefore exists for metal ion-containing dentifrice compositions which have reduced metallic taste and astringency, and which have improved resistance to phase separation.

SUMMARY

A first aspect of the present invention provides an oral care composition comprising: (a) one or more pyrophosphate compounds, wherein the total concentration of pyrophosphate compounds in the composition is 0.5 wt % to 1.5 wt %, based on the weight of the oral care composition; (b) one or more thickening gums, wherein the total concentration of thickening gums in the composition is 1.25 wt % to 1.6 wt %, based on the weight of the oral care composition; and (c) a metal ion source.

Optionally, the total concentration of pyrophosphate compounds in the composition is 0.75 wt % to 1.25 wt %, based on the weight of the oral care composition.

Optionally, the total concentration of pyrophosphate compounds in the composition is 0.9 wt % to 1.1 wt %, based on the weight of the oral care composition.

Optionally, the one or more pyrophosphate compounds comprises dialkali metal pyrophosphate salts, tetraalkali metal pyrophosphate salts, or any mixture of any two or more thereof.

Optionally, the one or more pyrophosphate compounds is selected from tetrasodium pyrophosphate (TSPP), tetrapotassium pyrophosphate (TKPP), and mixtures thereof.

Optionally, the one or more pyrophosphate compounds is a mixture of tetrasodium pyrophosphate and tetrapotassium pyrophosphate.

Optionally, tetrasodium pyrophosphate is present in a concentration of from 0.25 wt % to 0.75 wt %, based on the weight of the oral care composition, and tetrapotassium pyrophosphate is present in a concentration of from 0.25 wt % to 0.75 wt % based on the weight of the oral care composition.

Optionally, the total concentration of thickening gums in the composition is 1.25 wt % to 1.55 wt %, based on the weight of the oral care composition.

Optionally, the total concentration of thickening gums in the composition is 1.3 wt % to 1.5 wt %, based on the weight of the oral care composition.

Optionally, the one or more thickening gums is selected from carboxymethyl cellulose (CMC), sodium carboxymethyl cellulose, hydroxyethyl cellulose, xanthan gum, gum arabic, gellan gum, carrageenan, gum tragacanth, guar gum, gum karaya, or any mixture thereof.

Optionally, the one or more thickening gums comprises a mixture of carboxymethyl cellulose and xanthan gum.

Optionally, carboxymethyl cellulose is present in a concentration of 0.85 wt % to 1.2 wt % based on the weight of the oral care composition, and xanthan gum is present in a concentration of 0.4 wt % to 0.6 wt % based on the weight of the oral care composition.

Optionally, the metal ion source comprises a source of zinc ions, calcium ions, copper ions, iron ions, magnesium ions or manganese ions, or a combination of any two or more thereof.

Optionally, the metal ion source comprises a source of zinc ions.

Optionally, the source of zinc ions comprises at least one of zinc citrate, zinc lactate, zinc gluconate, zinc glycinate, zinc sulfate, zinc chloride, zinc malate, zinc tartrate, zinc carbonate, zinc phosphate or zinc oxide, or any mixture thereof.

Optionally, the metal ion source is present in an amount of from 0.5 wt % to 3 wt % based on the weight of the oral care composition.

Optionally, the metal ion source is present in an amount of from 1 wt % to 2 wt % based on the weight of the oral care composition.

Optionally, the source of zinc ions comprises a mixture of zinc oxide and zinc citrate.

Optionally, zinc citrate is present in an amount of from 0.25 wt % to 0.75 wt % based on the weight of the oral care composition and zinc oxide is present in an amount of 0.75 wt % to 1.25 wt % based on the weight of the oral care composition.

Optionally, the composition is a dentifrice in the form of a paste or gel.

In a second aspect, the present invention provides an oral care composition as defined above, having improved phase separation stability.

In a third aspect, the present invention provides for use of a combination of one or more pyrophosphate compounds with one or more thickening gums to reduce or prevent phase separation of an oral care composition which contains a metal ion source and the at least one pyrophosphate compound, wherein the total concentration of pyrophosphate compounds in the composition is 0.5 wt % to 1.5 wt %, based on the weight of the oral care composition and the total concentration of thickening gums in the composition is 1.25 wt % to 1.6 wt %, based on the weight of the oral care composition.

DETAILED DESCRIPTION

It should be understood that the detailed description and specific examples, while indicating embodiments of the invention, are intended for purposes of illustration only and are not intended to limit the scope of the invention.

As used throughout, ranges are used as shorthand for describing each and every value that is within the range. Any value within the range can be selected as the terminus of the range.

As referred to herein, all compositional percentages are by weight of the total composition unless otherwise indicated. As referred to herein, "ppm" (parts per million) refers to ppm by weight, unless otherwise indicated. As referred to herein, all ratios refer to weight ratios, unless otherwise indicated.

The terms "cosmetic stability" and "phase separation stability" as used herein refer to the ability of a dentifrice to resist phase separation into, for example, a liquid phase and a semi-solid phase. A composition having "increased phase separation stability" has an increased resistance to phase separation.

In some embodiments, the present invention provides an oral care composition comprising:
  a) one or more pyrophosphate compounds, wherein the total concentration of pyrophosphate compounds in the composition is 0.5 wt % to 1.5 wt %, based on the weight of the oral care composition;
  b) one or more thickening gums, wherein the total concentration of thickening gums in the composition is 1.25 wt % to 1.6 wt %, based on the weight of the oral care composition; and
  c) a metal ion source.

The oral care compositions of the present invention comprise one or more pyrophosphate compounds, wherein the total concentration of pyrophosphate compounds in the composition is 0.5 wt % to 1.5 wt % based on the weight of the oral care composition. For best taste and mouth feel, it is desirable to maintain the total pyrophosphate compound concentration about 0.5 wt %.

Optionally, the total concentration of pyrophosphate compounds in the composition may be from 0.6 wt % to 1.4 wt %, from 0.7 wt % to 1.3 wt %, from 0.75 wt % to 1.25 wt %, from 0.8 wt % to 1.2 wt %, from 0.9 wt % to 1.1 wt %, from 0.95 wt % to 1.05 wt %, or 1 wt %, all based on the weight of the oral care composition.

In some embodiments, the one or more pyrophosphate compounds comprises dialkali metal pyrophosphate salts, tetraalkali metal pyrophosphate salt, or any mixture of any two or more thereof.

In some embodiments, the one or more pyrophosphate compounds is selected from tetrasodium pyrophosphate (TSPP), tetrapotassium pyrophosphate (TKPP), and mixtures thereof.

In some embodiments, the one or more pyrophosphate compounds is a mixture of tetrasodium pyrophosphate (TSPP) and tetrapotassium pyrophosphate (TKPP). Optionally, tetrasodium pyrophosphate is present in a concentration of from 0.25 wt % to 0.75 wt %, based on the weight of the oral care composition, and tetrapotassium pyrophosphate is present in a concentration of from 0.25 wt % to 0.75 wt % based on the weight of the oral care composition. In some embodiments, TSPP is present in a concentration of from 0.3 wt % to 0.7 wt %, based on the weight of the oral care composition, and TKPP is present in a concentration of from 0.3 wt % to 0.7 wt %, based on the weight of the oral care composition. In some embodiments, TSPP is present in a concentration of from 0.4 wt % to 0.6 wt %, based on the weight of the oral care composition, and TKPP is present in a concentration of from 0.4 wt % to 0.6 wt %, based on the weight of the oral care composition. In some embodiments, TSPP is present in a concentration of from 0.45 wt % to 0.55 wt %, based on the weight of the oral care composition, and TKPP is present in a concentration of from 0.45 wt % to 0.55 wt %, based on the weight of the oral care composition. In some embodiments, TSPP is present in a concentration of 0.5 wt %, based on the weight of the oral care composition, and TKPP is present in a concentration of 0.5 wt %, based on the weight of the oral care composition.

The oral care compositions of the present invention also comprise one or more thickening gums, wherein the total concentration of thickening gums in the composition is 1.25 wt % to 1.6 wt %, based on the weight of the oral care composition.

In some embodiments, the total concentration of thickening gums in the composition is 1.25 wt % to 1.55 wt %, 1.3 wt % to 1.5 wt %, 1.35 wt % to 1.45 wt %, or 1.4 wt % based on the weight of the oral care composition.

In some embodiments, the one or more thickening gums is selected from carboxymethyl cellulose (CMC), sodium carboxymethyl cellulose, hydroxyethyl cellulose, xanthan gum, gum arabic, gellan gum, carrageenan (also known as Irish moss; particularly i-carrageenan i.e. iota-carrageenan), gum tragacanth, guar gum, gum karaya, or any mixture thereof.

In some embodiments, the one or more thickening gums comprises a mixture of carboxymethyl cellulose and xanthan gum.

Optionally, carboxymethyl cellulose (CMC) is present in a concentration of 0.85 wt % to 1.2 wt % based on the weight of the oral care composition, and xanthan gum is present in a concentration of 0.4 wt % to 0.6 wt % based on the weight of the oral care composition. In some embodiments, CMC is present in a concentration of 0.85 wt % to 1.1 wt % based on the weight of the oral care composition, and xanthan gum is present in a concentration of 0.45 wt % to 0.55 wt % based on the weight of the oral care composition. In some embodiments, CMC is present in a concentration of 0.875 wt % to 1.0 wt % based on the weight of the oral care composition, and xanthan gum is present in a concentration of 0.475 wt % to 0.525 wt % based on the weight of the oral care composition. In some embodiments, CMC is present in a concentration of 0.9 wt % based on the weight of the oral care composition, and xanthan gum is present in a concentration of 0.5 wt % based on the weight of the oral care composition.

The oral care compositions of the present invention further comprise a metal ion source. In some embodiments, the metal ion source is present in an amount of from 0.5 wt % to 3 wt %, 0.75 wt % to 2.5 wt %, 1 wt % to 2 wt %, 1.25 wt % to 1.75 wt %, 1.3 wt % to 1.7 wt %, 1.4 wt % to 1.6 wt %, 1.45 wt % to 1.55 wt %, or 1.5 wt % based on the weight of the oral care composition.

In some embodiments, the metal ion source comprises a source of zinc ions, calcium ions, copper ions, iron ions, magnesium ions or manganese ions, or a combination of any two or more thereof.

In some embodiments, the metal ion source comprises a source of zinc ions.

In some embodiments, the source of zinc ions comprises at least one of zinc citrate, zinc lactate, zinc gluconate, zinc glycinate, zinc sulfate, zinc chloride, zinc malate, zinc tartrate, zinc carbonate, zinc phosphate or zinc oxide, or any mixture thereof.

In some embodiments, the source of zinc ions comprises a mixture of zinc oxide (ZnO) and zinc citrate. In some embodiments, zinc citrate is present in an amount of from 0.25 wt % to 0.75 wt % based on the weight of the oral care composition and zinc oxide is present in an amount of 0.75 wt % to 1.25 wt % based on the weight of the oral care composition. In some embodiments, zinc citrate is present in an amount of from 0.3 wt % to 0.7 wt % based on the weight of the oral care composition and zinc oxide is present in an amount of 0.8 wt % to 1.2 wt % based on the weight of the oral care composition. In some embodiments, zinc citrate is present in an amount of from 0.4 wt % to 0.6 wt % based on the weight of the oral care composition and zinc oxide is present in an amount of 0.9 wt % to 1.1 wt % based on the weight of the oral care composition. In some embodiments, zinc citrate is present in an amount of from 0.45 wt % to 0.55 wt % based on the weight of the oral care composition and zinc oxide is present in an amount of 0.95 wt % to 1.05 wt % based on the weight of the oral care composition. In some embodiments, zinc citrate is present in an amount of 0.5 wt % based on the weight of the oral care composition and zinc oxide is present in an amount of 1.0 wt % based on the weight of the oral care composition. In vitro biofilm reduction studies have shown that dentifrice prototypes containing 1 wt % zinc oxide and 0.5 wt % zinc citrate give particularly good bacterial kill effectiveness.

In some embodiments, the oral care composition is a dentifrice in the form of a paste or gel.

The present invention also provides an oral care composition as described above having improved phase separation stability.

The present invention also provides for use of a combination of one or more pyrophosphate compounds with one or more thickening gums to reduce or prevent phase separation of an oral care composition which contains a metal ion source and the at least one pyrophosphate compound, wherein the total concentration of pyrophosphate compounds in the composition is 0.5 wt % to 1.5 wt %, based on the weight of the oral care composition and the total concentration of thickening gums in the composition is 1.25 wt % to 1.6 wt %, based on the weight of the oral care composition.

In some embodiments, the oral care compositions of the present invention may comprise one or more agents selected from abrasives, diluents, bicarbonate salts, pH modifying agents, surfactants, foam modulators, additional thickening agents, viscosity modifiers, humectants, sweeteners, flavorants, pigments, antibacterial agents, anticaries agents, anticalculus or tartar control agents, and mixtures thereof.

The compositions of the present invention may include water in an amount of from about 0.5 wt % to about 25 wt %, optionally about 2.0 wt % to about 22 wt %, further optionally about 5 wt % to about 20 wt %.

In some embodiments, the compositions of the present invention further comprise an abrasive.

Abrasives that may be used include silica abrasives such as precipitated or hydrated silicas having a mean particle size of up to about 20 microns, such as Zeodent 105 and Zeodent 114 marketed by J.M. Huber Chemicals Division, Havre de Grace, Md. 21078, or Sylodent 783 marketed by Davison Chemical Division of W.R. Grace & Company. Abrasives such as Sorbosil AC 43 from PQ Corporation may also be included. Other useful dentifrice abrasives include aluminium oxide, aluminum silicate, calcined alumina, bentonite or other siliceous materials, insoluble phosphates, calcium carbonate, and mixtures thereof.

The abrasive may be present in an amount of from 5 to 38 wt % based on the weight of the composition, optionally from 10 to 20 wt % based on the weight of the composition.

In some embodiments, the oral care compositions of the present invention comprise at least one bicarbonate salt, useful for example to impart a "clean feel" to teeth and gums due to effervescence and release of carbon dioxide. Any orally acceptable bicarbonate can be used, including without limitation, alkali metal bicarbonates such as sodium and potassium bicarbonates, ammonium bicarbonate and the like. One or more bicarbonate salts are optionally present in a total amount of about 0.1 wt % to about 50 wt %, for example about 1 wt % to 20 wt %, by total weight of the composition.

In some embodiments, the compositions of the present invention comprise at least one pH modifying agent. Such agents include acidifying agents to lower pH, basifying agents to raise pH, and buffering agents to control pH within a desired range. For example, one or more compounds selected from acidifying, basifying and buffering agents can be included to provide a pH of 2 to 10, or in various illustrative embodiments, 2 to 8, 3 to 9, 4 to 8, 5 to 7, 6 to 10, 7 to 9, etc. Any orally acceptable pH modifying agent can be used, including without limitation, carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate), imidazole and the like. One or more pH modifying agents are optionally present in a total amount effective to maintain the composition in an orally acceptable pH range.

In a still further embodiment, the compositions of the invention comprise at least one surfactant. Any orally acceptable surfactant, most of which are anionic, nonionic or amphoteric, can be used. Suitable anionic surfactants include without limitation, water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation, poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation, derivatives of $C_{8-20}$ aliphatic secondary and tertiary amines having an anionic group such as carboxylate, sulfate, sulfonate, phosphate or phosphonate. Betaines may also be used, a suitable example of which is cocoamidopropyl betaine. One or more surfactants are optionally present in a total amount of about 0.01 wt % to about 10 wt %, for example, from about 0.05 wt % to about 5 wt %, or from about 0.1 wt % to about 2 wt % by total weight of the composition.

In some embodiments, the compositions of the invention comprise at least one foam modulator, useful for example to increase amount, thickness or stability of foam generated by the composition upon agitation. Any orally acceptable foam modulator can be used, including without limitation, polyethylene glycols (PEGs), also known as polyoxyethylenes. High molecular weight PEGs are suitable, including those having an average molecular weight of 200,000 to 7,000,000, for example 500,000 to 5,000,000, or 1,000,000 to 2,500,000. One or more PEGs are optionally present in a total amount of about 0.1 wt % to about 10 wt %, for example from about 0.2 wt % to about 5 wt %, or from about 0.25 wt % to about 2 wt %, by total weight of the composition.

In some embodiments, the compositions of the present invention comprise at least one additional thickening agent, useful for example to impart a desired consistency and/or mouth feel to the composition. Any orally acceptable thickening agent can be used, including without limitation, carbomers, also known as carboxyvinyl polymers, colloidal magnesium aluminum silicate, colloidal silica and the like.

A preferred class of additional thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol® series. Particularly preferred Carbopols include Carbopol 934, 940, 941, 956, 974P, and mixtures thereof. Silica thickeners such as DT 267 (from OSC—Lianji Chemical Industry Co., Ltd.) may also be used. One or more additional thickening agents are optionally present in a total amount of from about 0.01 wt % to 15 wt %, for example from about 0.1 wt % to about 10 wt %, or from about 0.2 wt % to about 5 wt %, by total weight of the composition.

In some embodiments, the compositions of the invention comprise at least one viscosity modifier, useful for example to help inhibit settling or separation of ingredients or to promote re-dispersibility upon agitation of a liquid composition. Any orally acceptable viscosity modifier can be used, including without limitation, mineral oil, petrolatum, clays and organomodified clays, silica and the like. One or more viscosity modifiers are optionally present in a total amount of from about 0.01 wt % to about 10 wt %, for example, from about 0.1 wt % to about 5 wt %, by total weight of the composition.

In some embodiments, the compositions of the invention comprise at least one humectant. Any orally acceptable humectant can be used, including without limitation, polyhydric alcohols such as glycerin, sorbitol (particularly as a 70% solution), xylitol or low molecular weight polyethylene glycols (PEGs). Most humectants also function as sweeteners. One or more humectants are optionally present in a total amount of from about 1 wt % to about 70 wt %, for example, from about 1 wt % to about 50 wt %, from about 2 wt % to about 25 wt %, or from about 5 wt % to about 15 wt %, by total weight of the composition.

In some embodiments, a composition of the present invention comprises at least one sweetener, useful for example to enhance taste of the composition. Any orally acceptable natural or artificial sweetener can be used, including without limitation dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof (such as sodium saccharin), dipeptide-based intense sweeteners, cyclamates and the like. One or more sweeteners are optionally present in a total amount depending strongly on the particular sweetener(s) selected, but typically 0.005 wt % to 5 wt %, by total weight of the composition, optionally 0.005 wt % to 0.2 wt %, further optionally 0.05 wt % to 0.1 wt % by total weight of the composition.

In some embodiments, a composition of the present invention comprises at least one flavorant, useful for example to enhance taste of the composition. Any orally acceptable natural or synthetic flavorant can be used, including without limitation tea flavours (such as Cool Jasmine Tea Flavour), vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., and other flavours; adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of from about 0.01 wt % to about 5 wt %, for example, from about 0.03 wt % to about 2.5 wt %, optionally about 0.05 wt % to about 1.5 wt %, further optionally about 0.1 wt % to about 0.3 wt % by total weight of the composition.

A composition of the invention may comprise at least one colorant. Colorants herein include pigments, dyes, lakes and agents imparting a particular luster or reflectivity such as pearling agents. Any orally acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, Blue #1 1.25% solution, and the like. One or more colorants are optionally present in a total amount of from about 0.001 wt % to about 20 wt %, for example, from about 0.01 wt % to about 10 wt %, or from about 0.1 wt % to about 5 wt %, by total weight of the composition.

The compositions of the present invention optionally comprise an antibacterial or preservative agent, such as chlorhexidine, triclosan, quaternary ammonium compounds (for example benzalkonium chloride) or parabens such as methylparaben or propylparaben. One or more antibacterial or preservative agent is optionally present in the composition in a total amount of from about 0.01 wt % to about 0.5 wt %, optionally about 0.05 wt % to about 0.1 wt % by total weight of the composition.

In some embodiments, the composition comprises a fluoride ion source. Fluoride ion sources include, but are not limited to: stannous fluoride, sodium fluoride, potassium fluoride, potassium monofluorophosphate, sodium monofluorophosphate, ammonium monofluorophosphate, sodium fluorosilicate, ammonium fluorosilicate, amine fluoride such as olaflur (N'-octadecyltrimethylendiamine-N,N,N-tris(2-ethanol)-dihydrofluoride), ammonium fluoride, and combinations thereof. In certain embodiments the fluoride ion source includes stannous fluoride, sodium fluoride, amine fluorides, sodium monofluorophosphate, as well as mixtures thereof. In certain embodiments, the oral care composition of the invention may also contain a source of fluoride ions or fluorine-providing ingredient in amounts sufficient to supply about 50 to about 5000 ppm fluoride ion, e.g., from about 100 to about 1000, from about 200 to about 500, or about 250 ppm fluoride ion. Fluoride ion sources may be added to the compositions of the invention at a level of about 0.001 wt % to about 10 wt %, e.g., from about 0.003 wt % to about 5 wt %, 0.01 wt % to about 1 wt, or about 0.05 wt %. However, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride.

Some embodiments of the present invention provide compositions having an N value of less than 1.5. Other embodiments provide compositions having an N value less than 1. Further embodiments provide compositions having an N value of less than 0.5. Yet other embodiments provide compositions having an N value of less than 0.1.

The composition of the present invention optionally comprises a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The composition of the present invention optionally incorporates one or more antisensitivity agents, e.g., potassium salts such as potassium nitrate, potassium bicarbonate, potassium chloride, potassium citrate, and potassium oxalate; capsaicin; eugenol; strontium salts; chloride salts and combinations thereof. Such agents may be added in effective amounts, e.g., from about 1 wt % to about 20 wt % by weight based on the total weight of the composition, depending on the agent chosen. The compositions of the present invention may also be used to treat hypersensitivity by blocking dentin tubules when applied to a tooth.

In some embodiments, the composition of the invention further comprises an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The composition of the present invention may additionally optionally comprise a tartar control (anticalculus) agent as provided below. Tartar control agents among those useful herein include salts of the specified agents, including alkali metal and ammonium salts. The agents include: phosphates and polyphosphates, polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, sodium trimetaphosphate, sodium hexametaphosphate and mixtures thereof. Other useful tartar control agents include polycarboxylate polymers and polyvinyl methyl ether/maleic anhydride (PVM/MA) copolymers, such as GANTREZ®.

In some embodiments, the composition of the present invention further comprises a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophan, L-lysine, methionine, threonine, levocarnitine and L-carnitine), lipotropics (such as choline, inositol, betaine, and linoleic acid), and mixtures thereof.

For a dentifrice composition containing 1 wt % zinc oxide and 0.5 wt % zinc citrate, the addition of 1 wt % TSPP and 1 wt % TKPP has been perceived to improve taste and mouthfeel. A combination of CMC and xanthan gum in concentrations of 0.8 wt % and 0.3 wt %, respectively, is commonly used in dentifrice compositions in order to provide structure and desired aesthetics to the composition. However, the present inventors have observed that, in a dentifrice composition which contains 1 wt % zinc oxide and 0.5 wt % zinc citrate in combination with 1 wt % TSPP and 1 wt % TKPP, phase separation occurs immediately after formation of the dentifrice composition if the commonly-used thickening system of 0.8 wt % CMC and 0.3 wt % xanthan gum is employed, in a high sorbitol silica formula. This separation was observed to become more severe during aging at both 40° C. and −10° C.

Without wishing to be bound by any theory, it is thought that the relatively high level of 2 wt % total pyrophosphate compounds is responsible for disrupting the structure of the dentifrice, and that the thickening system of 0.8 wt % CMC and 0.3 wt % xanthan gum does not provide enough structure to maintain the dentifrice in a single phase. However, as will be discussed below, the present inventors have found that simply increasing the concentration of the gums alone did not improve the phase separation stability; and that simply decreasing the concentration of the pyrophosphates alone also did not improve the phase separation stability. In fact, the present inventors have found that simply increasing the gum concentration or decreasing the pyrophosphate concentration alone further decreased the phase separation stability. However, the present inventors have surprisingly found that increasing the gum concentration together with decreasing the pyrophosphate concentration actually increased the phase separation stability of the dentifrice compositions.

Examples

A series of studies showed that a marked improvement in phase separation stability could be achieved if the total concentration of carboxymethyl cellulose and xanthan gum in an oral care composition was increased from 1.1 wt % to 1.4 wt %, and if the total concentration of tetrasodium pyrophosphate and tetrapotassium pyrophosphate in the composition was simultaneously decreased from 2 wt % to 1.5 wt %. The studies showed that, while the phase separation stability was drastically improved, the taste and mouth feel of the composition remained acceptable.

Formulations A to E were prepared, as detailed in Table 1, below. Of these, Formulation A corresponds to the original formula containing 1 wt % TKPP, 1 wt % TSPP, 0.8 wt % carboxymethyl cellulose (CMC) and 0.3 wt % xanthan gum. In Formulation B, the concentration of TKPP and TSPP were kept the same as in Formulation A, but the concentration of CMC was increased to 0.9 wt % and the concentration of xanthan gum was increased to 0.5 wt %. In Formulation C, the concentration of xanthan gum and CMC was kept the same as in Formulation A, but the concentrations of TKPP and TSPP were reduced to 0.7 wt % and 0.5 wt %, respectively. In Formulations D and E, the concentrations of TKPP and TSPP were each reduced to 0.5 wt % and the concentrations of CMC and xanthan gum were increased to 0.9 wt % and 0.5 wt %, respectively.

TABLE 1

|  | A (wt %) | B (wt %) | C (wt %) | D (wt %) | E (wt %) |
| --- | --- | --- | --- | --- | --- |
| Water | 13.3 | 13 | 14.1 | 14.1 | 14 |
| Sorbitol-70% solution | 55 | 55 | 55 | 55 | 55 |
| Polyethylene Glycol 600 | 2 | 2 | 2 | 2 | 2 |
| Sodium saccharin | 0.3 | 0.3 | 0.3 | 0.3 | 0.3 |
| AC 43 abrasive | 5 | 5 | 5 | 5 | 5 |
| ZnO | 1 | 1 | 1 | 1 | 1 |

TABLE 1-continued

|  | A (wt %) | B (wt %) | C (wt %) | D (wt %) | E (wt %) |
|---|---|---|---|---|---|
| Zinc Citrate | 0.5 | 0.5 | 0.5 | 0.5 | 0.5 |
| TSPP | 1 | 1 | 0.7 | 0.5 | 0.5 |
| TKPP | 1 | 1 | 0.5 | 0.5 | 0.5 |
| CMC 2000 S | 0.8 | 0.9 | 0.8 | 0.9 | 0.9 |
| Xanthan Gum | 0.3 | 0.5 | 0.3 | 0.5 | 0.5 |
| Sodium monofluorophosphate | 1.1 | 1.1 | 1.1 | 1.1 | 1.1 |
| Silica abrasive Zeo 114 | 10 | 10 | 10 | 10 | 10 |
| Silica thickener DT 267 | 4 | 4 | 4 | 4 | 4 |
| Sodium lauryl sulfate | 2 | 2 | 2 | 2 | 2 |
| Cocamidopropyl betaine | 1.25 | 1.25 | 1.25 | 1.25 | 1.25 |
| Flavor 1 | 1.3 | 1.3 | 1.3 | — | 1.3 |
| Flavor 2 | — | — | — | 1.2 | — |
| Blue #1-1.25% solution | 0.15 | 0.15 | 0.15 | 0.15 | 0.15 |
| TOTAL | 100 | 100 | 100 | 100 | 100 |

Phase separation of a composition can be predicted using a centrifugation method. Samples are centrifuged using an analytical centrifuge (LumiSizer 110 from L.U.M. GmbH, Berlin), which measures separation of the product by measuring optical transmission through the tube as a function of time. The centrifugation method generates a number known as the "wall liquid separation scale number", N. Sample stability is considered as acceptable when N≤3 and unacceptable when N>3. The lower the N value, the more robust the formula (i.e. the higher its resistance to phase separation). Most often, a value of N which is less than 1.5 is necessary to ensure a greater confidence in predicting real time stability.

The centrifugation method was used to predict the likelihood of phase separation for each of the formulations A to E above for 3 years shelf life at ambient temperature. The wall liquid separation scale number was calculated for each of these formulations, and the results are shown below in Table 2 (below):

TABLE 2

|  | A (wt %) | B (wt %) | C (wt %) | D (wt %) | E (wt %) |
|---|---|---|---|---|---|
| Wall separation scale number, N | 1.94 | 3.55 | 3.72 | 0.07 | 0.07 |

As can be seen in Table 2, simply increasing the concentration of the thickening gum (Formulation B) or simply decreasing the concentration of the pyrophosphates (Formulation C) as compared to the original Formulation A in fact decreased the phase separation stability of the compositions (as shown by the increase in N value for Formulations B and C as compared to Formulation A). This high N value for Formulations B and C indicates that these compositions will phase separate and result in a product which is not shelf stable.

However, both Formulations D and E (in which the concentration of thickening gum was increased and the concentration of pyrophosphates was decreased as compared to Formulation A) have a very low wall separation scale number of N=0.07, indicating that these formulations will provide an acceptable level of phase separation.

A real-time accelerated aging study of Formulation D and E showed that there was no phase separation of these compositions for up to 6 months, confirming the prediction of the centrifugation method. In contrast, Formulation A failed the real-time accelerated aging test.

It was also found that the taste and mouth feel of the compositions containing a total concentration of 1.4 wt % CMC and xanthan gum, and a total concentration of 1.5 wt % TSPP and TKPP were acceptable.

Whilst particular embodiments of the invention have been illustrated and described, it will be obvious to those skilled in the art that various changes and modifications may be made without departing from the scope of the invention as defined in the appended claims.

The invention claimed is:

1. An oral care composition comprising:
   a) one or more pyrophosphate compounds, wherein the total concentration of pyrophosphate compounds in the composition is 0.5 wt % to 1 wt %, of the composition, wherein the one or more pyrophosphate compounds is selected from tetrasodium pyrophosphate (TSPP), tetrapotassium pyrophosphate (TKPP), and a combination thereof;
   b) one or more thickening gums, wherein the total concentration of thickening gums in the composition is 1.25 wt % to 1.6 wt %, of the composition, wherein the one or more thickening gums comprises a mixture of carboxymethyl cellulose and xanthan gum; and
   c) a metal ion source, wherein the source of metal ions comprises a mixture of zinc oxide and zinc citrate.

2. The composition according to claim 1, wherein the one or more pyrophosphate compounds is a mixture of tetrasodium pyrophosphate and tetrapotassium pyrophosphate.

3. The composition according to claim 2, wherein tetrasodium pyrophosphate is present in a concentration of from 0.25 wt % to 0.75 wt %, based on the weight of the oral care composition, and tetrapotassium pyrophosphate is present in a concentration of from 0.25 wt % to 0.75 wt % based on the weight of the oral care composition.

4. The composition according to claim 1, wherein the total concentration of thickening gums in the composition is 1.25 wt % to 1.55 wt %, based on the weight of the oral care composition.

5. The composition according to claim 4, wherein the total concentration of thickening gums in the composition is 1.3 wt % to 1.5 wt %, based on the weight of oral care composition.

6. The composition according to claim 1, wherein carboxymethyl cellulose is present in a concentration of 0.85 wt % to 1.2 wt % based on the weight of the oral care composition, and xanthan gum is present in a concentration of 0.4 wt % to 0.6 wt % based on the weight of the oral care composition.

7. The composition according to claim 1, wherein the metal ion source is present in an amount of from 0.5 wt % to 3 wt % based on the weight of the oral care composition.

8. The composition according to claim 7, wherein the metal ion source is present in an amount of from 1 wt % to 2 wt % based on the weight of the oral care composition.

9. The composition according to claim 1, wherein zinc citrate is present in an amount of from 0.25 wt % to 0.75 wt % based on the weight of the oral care composition and zinc oxide is present in an amount of 0.75 wt % to 1.25 wt % based on the weight of the oral care composition.

10. The composition according to claim 1, wherein the composition is a dentifrice in the form of a paste or gel.

11. The composition according to claim 1, having improved phase separation stability.

12. The composition according to claim 1, wherein the ratio of pyrophosphate compounds to thickening gums is less than 1:1.

13. The composition according to claim 1, wherein the ratio of pyrophosphate compounds to thickening gums is less than 0.99.

14. The composition claim 1, wherein the ratio of pyrophosphate compounds to thickening gums is less than 0.8.

15. The composition according to claim 1, wherein the ratio of pyrophosphate compounds to thickening gums is less than 0.75.

16. The composition according to claim 1, wherein the N value is less than 1.5.

17. The composition according to claim 1, wherein zinc citrate is present in an amount of 0.5 wt % based on the weight of the oral care composition and zinc oxide is present in an amount of 1.0 wt % based on the weight of the oral care composition.

* * * * *

UNITED STATES PATENT AND TRADEMARK OFFICE
CERTIFICATE OF CORRECTION

| | |
|---|---|
| PATENT NO. | : 11,253,446 B2 |
| APPLICATION NO. | : 16/719693 |
| DATED | : February 22, 2022 |
| INVENTOR(S) | : Yun Xu et al. |

It is certified that error appears in the above-identified patent and that said Letters Patent is hereby corrected as shown below:

In the Claims

In Column 13, Line 4, in Claim 14, before "claim 1,", insert -- according to --.

Signed and Sealed this
Twenty-fourth Day of May, 2022

Katherine Kelly Vidal
*Director of the United States Patent and Trademark Office*